United States Patent [19]
Yoshida et al.

[11] Patent Number: 4,624,768
[45] Date of Patent: Nov. 25, 1986

[54] ELECTROPHORESIS APPARATUS

[75] Inventors: Motoko Yoshida, Chofu; Michio Itoh, Kokubunji; Kunihiro Maeda, Hitachi, all of Japan

[73] Assignee: Hitachi, Ltd., Tokyo, Japan

[21] Appl. No.: 695,006

[22] Filed: Jan. 25, 1985

[30] Foreign Application Priority Data

Jan. 25, 1984 [JP] Japan .................... 59-10034

[51] Int. Cl.$^4$ ............................ G01N 27/28
[52] U.S. Cl. .................. 204/299 R; 204/182.8
[58] Field of Search ............ 204/299 R, 301, 180 G, 204/182.8

[56] References Cited

FOREIGN PATENT DOCUMENTS 57-49852  3/1982  Japan .................... 204/182.8

Primary Examiner—John F. Niebling
Assistant Examiner—B. J. Boggs, Jr.
Attorney, Agent, or Firm—Antonelli, Terry & Wands

[57] ABSTRACT

A horizontal electrophoresis apparatus characterized by a cooling plate which consists of a sintered SiC with high thermal conductivity and good insulating properties, or sintered material composed mainly of SiC, and a Peltier element, as the heat conducting material to cool the supporting matrix or electrolyte.

3 Claims, 6 Drawing Figures

ELECTROPHORESIS APPARATUS

BACKGROUND OF THE INVENTION

The present invention relates to an electrophoresis apparatus and more specifically to a horizontal electrophoresis apparatus.

Conventional electrophoresis apparatus, as described in a book titled "Isoelectric Focusing and Isotachophoresis" (published by Kyoritsu Shuppan in 1980) on page 71 and 72, has a water jacket cooling plate through which water, cooled by a separate device, is passed. This is indirect cooling which does not follow variation in the amount of heat generated in the supporting matrix for electrophoresis and therefore has the drawback that temperature control of the supporting matrix is difficult to accomplish when electrophoresis is performed at high voltages.

SUMMARY OF THE INVENTION

The object of this invention is to provide an improved electrophoresis apparatus. Another object of the invention is to provide an electrophoresis apparatus which cools according to the amount of heat generated.

These objectives are achieved by a horizontal electrophoresis apparatus in which a cooling plate which comprises sintered SiC, or sintered material composed mainly of SiC, and a Peltier element is in the lower part of the supporting matrix for electrophoresis to cool the supporting matrix.

DETAILED DESCRIPTION OF PREFERRED EMBODIMENTS

Horizontal electrophoresis is a process to move and separate, through the effect of an electric field, a sample applied to a slot cut in a supporting matrix such as polyacrylamide gel put horizontally on a cooling plate with the extream ends of the gel in contact with electrolytes. When current flows, heat is generated in the gel, causing denaturation of proteins and convection of buffer solution or electrolyte contained in the gel, which in turn results in disturbance in the electrophoretogram or electrophoretic pattern. It is therefore desired that the cooling plate can measure temperature variations of the gel and thereby cool it to a specified constant temperature. The application to clinical diagnosis of the protein separation technique has created a demand for faster electrophoresis at higher voltages. Also, greater emphasis is being placed on the need for reproducibility of the electrophoretic pattern. To meet these requirements, the electrophoresis apparatus must employ a direct cooling method which measures and feeds back the gel temperature for temperature control, and the cooling plate material that contacts the gel must have high thermal conductivity, excellent insulating properties and great resistance to chemical corrosion. As a result of an investigation of the characteristic values of various materials, a sintered SiC with high thermal conductivity and excellent insulating properties has been chosen as an optimum material and is being used in combination with the Peltier element. The sintered SiC is obtained by adding 0.1 to 3.5 wt % BeO or preferably 0.5 to 2 wt % BeO to alpha type SiC powder and by sintering the mixture in a hot-press [2,000°–2,100° C., 29 MPa (300 kg/cm$^2$), for 0.5 to 2 hours]. The sintered SiC thus obtained is characterized by high density (95% or more of theoretical density), high thermal conductivity, excellent electrical insulating properties, and a thermal expansion coefficient almost equal to that of Si, all of which cannot be attained with a single conventional material.

TABLE 1

Comparison of characteristics between SiC ceramics with high heat conductivity and insulation and other materials

| Material | Heat conductivity (W/m · K) | Thermal expansion coefficient (× 10$^{-6}$/°C.) | Electrical resistance (Ω · cm) | Dielectric constant (1 MHz) |
|---|---|---|---|---|
| SiC ceramics with high conductivity and insulation | 270 | 3.7 | >4 × 10$^{13}$ | 42 |
| Alumina | 20 | 6.7–7.5 | >10$^{14}$ | 8–10 |
| Beryllia | 240 | 8.0 | >10$^{14}$ | 6–8 |
| Aluminum | 230 | 25.7 | 2.7 × 10$^{-6}$ | — |
| Single crystal Si | 125 | 3.5–4.0 | — | 12 |

The sintered material shown in the above table is introduced in Japanese Patent Publication No. 58-31755. It is also possible to use sintered material described in the Japanese Patent Laid-Open No. 57-2591.

Now, one embodiment of this invention will be described with reference to FIGS. 1 to 6.

Embodiment 1

Figure 1:
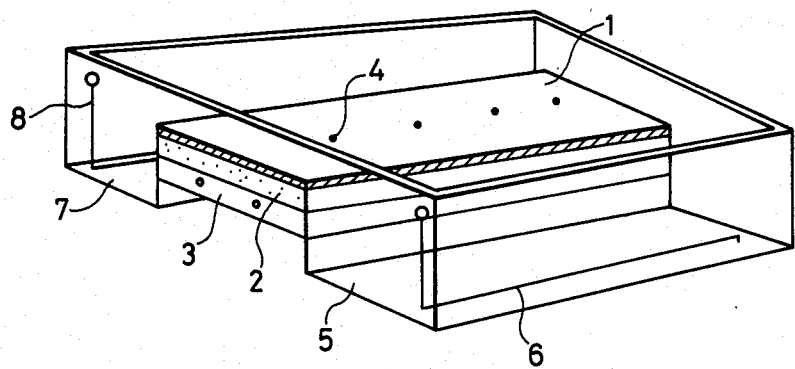
FIG. 1 is a perspective view of an electrophoresis apparatus of this invention.
Figure 2:
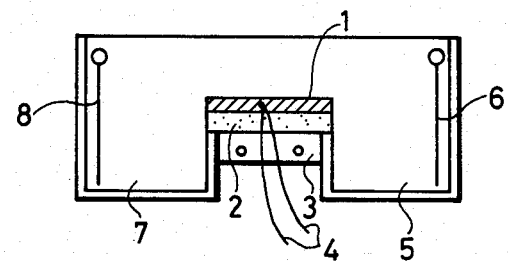
FIG. 2 is a vertical cross section of FIG. 1.
Figure 3:
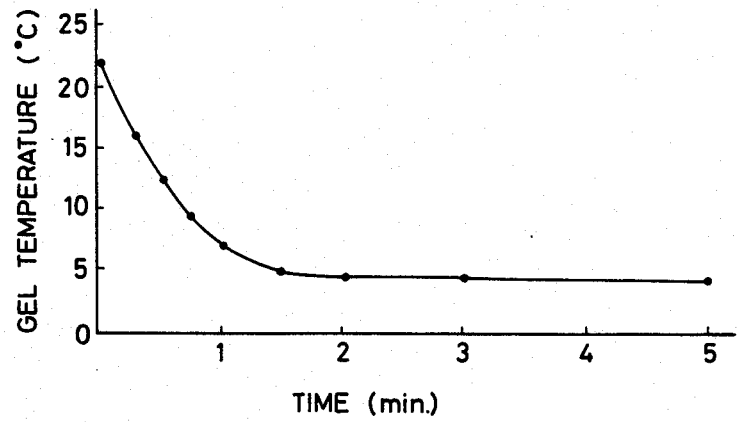
FIG. 3 is cooling characteristics when the temperature setting (4° C.) is entered.

A silanized glass plate to which a polyacrylamide gel is bound (10×10×0.05 cm) is mounted on the cooling plate of the horizontal electrophoresis apparatus with the glass plate facing down. The cooling plate 1 of SiC with high thermal conductivity and good insulating properties is integrated with the Peltier element 2 which has a heat dissipating plate 3. A thermistor 4 is put on the cooling plate surface or built into the SiC plate near the surface. The electrophoresis is performed as follows. A gel bound to a silanized glass plate is placed on the cooling plate and is connected with electrolytes by paper bridges. After a sample is placed in position, the power supply is turned on to start the electrophoresis process in which the sample is moved and at the same time the gel is heated. The raised temperature is measured by the built-in thermistor and is fed back to the Peltier element power supply to regulate the gel temperature to a setting temperature (for example, 4° C.). By combining the SiC plates (17×10×0.5 cm) with the Peltier elements (which can absorb 14 W at 3.5 V, 25 A) and using four combinations, it is possible to perform the electrophoresis with five gels at one time. Temperature variation of gel with the Peltier power supply turned on is shown in FIG. 3. One or two minutes after power has been applied, the gel temperature decreases to a specified level, the heat absorption here being equivalent to about 10 W from each gel, thus providing electrophoretic patterns which can be easily reproduced. The time required for electrophoresis has been reduced from five hours required with the conventional indirect cooling method to only two hours in this embodiment.

Embodiment 2

Figure 4:
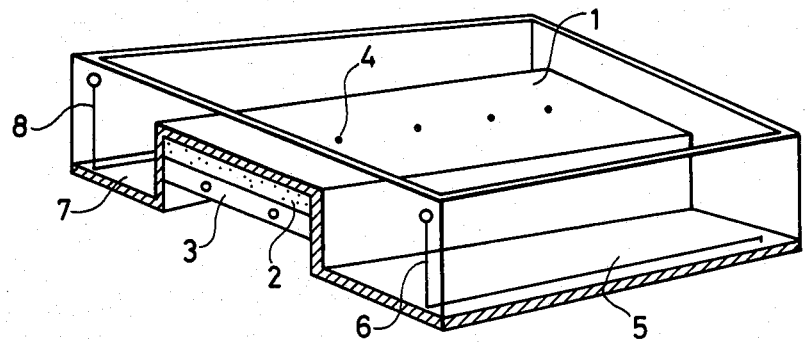
FIG. 4 is a perspective view of an electrophoresis apparatus which cools the cooling plate and the electrolyte simultaneously.
Figure 5:
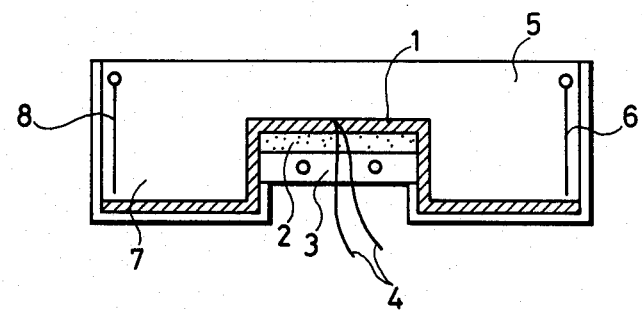
FIG. 5 is a vertical cross section of FIG. 4.
Figure 6:
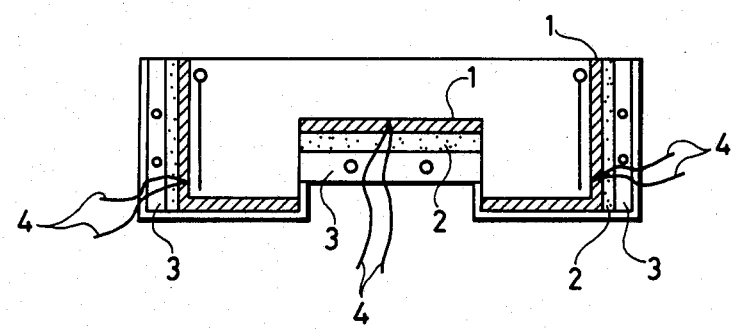
FIG. 6 is a vertical cross section of an electrophoresis apparatus which controls the temperature of the cooling plate and the electrolyte separately.

In the first embodiment, when the difference between the setting temperature and the ambient temperature is great, drops of water condense on the cooled gel surface due to the saturated vapor pressure difference between the cooling portion and the electrolyte. This often results in an electrophoretic pattern artifact. FIGS. 4 and 5 show the SiC cooling plate 1 immersed in electrolyte to cool the electrolyte at the same time. FIG. 6 shows independent cooling elements (each consisting of SiC plate, Peltier element and temperature sensor) to perform strict temperature control on the cooling plate and electrolyte. With this embodiment it is possible to perform electrophoresis quickly at room temperature without the process being adversely affected by ambient temperature.

In this invention SiC ceramics with high thermal conductivity and insulation, combined with the Peltier element, are used in the cooling element for electrophoresis. According to this invention, because of the high thermal conductivity of SiC, the temperature stabilizes to the setting value within a short time (1 or 2 minutes) after the temperature is set. Good cooling efficiency brought about by high thermal conductivity makes it possible to absorb a large quantity of heat generated in the gel (say, 100 mW for each unit area (cm$^2$) of the gel), thereby helping to reduce the time required for electrophoresis. Furthermore, since the gel temperature is measured by a sensor provided on the gel surface or in the SiC plate in contact with the gel and then fed back to the power supply through SiC, the gel is directly cooled, exhibiting good response characteristics, and electrophoresis can be performed in a uniform manner (for example, at 4° C. and 500 V). This in turn makes it possible to obtain reproducible electrophoretic patterns even for such complicated separation pattern as serum proteins. With the high thermal conductivity and good insulating properties of the SiC plate being taken advantage of, it is also possible to cool an object (for instance, solution) remote from the Peltier element, too. This means simultaneous cooling of the cooling plate and the electrolyte, contributing to reduction in size of the electrophoresis apparatus. Also, if the electrolyte should spill on the cooling plate, there will be no shortcircuit; the apparatus will continue functioning normally.

We claim:

1. A horizontal electrophoresis apparatus which comprises a supporting matrix for electrophoresis, a cooling plate formed of sintered SiC for supporting said matrix, and a peltier element for cooling said cooling plate; said sintered SiC comprising mainly alpha-type SiC and containing 0.1 to 3.5 wt. % of beryllia or boron nitride.

2. A horizontal electrophoresis apparatus as defined in claim 1, in which the sintered SiC exhibits a specific resistance of $10^{10} \Omega$.cm or more at room temperature and thermal conductivity of 0.4 cal/cm.sec.° C. or more at room temperature.

3. A horizontal electrophoresis apparatus as defined in claim 1, in which the sintered SiC plate extends into an anolyte vessel and a catholyte vessel to cool anolyte and catholyte in addition to the supporting matrix for electrophoresis.

* * * * *